United States Patent
Jean et al.

(10) Patent No.: US 6,614,238 B1
(45) Date of Patent: Sep. 2, 2003

(54) MICROWAVE SENSOR HAVING IMPROVED SENSITIVITY

(75) Inventors: Buford Randall Jean, Round Rock, TX (US); Frederick Lynn Whitehead, Austin, TX (US); John Lee Daniewicz, Austin, TX (US)

(73) Assignee: Rhino Analytics, L.L.C., Austin, TX (US)

( * ) Notice: Subject to any disclaimer, the term of this patent is extended or adjusted under 35 U.S.C. 154(b) by 22 days.

(21) Appl. No.: 09/716,748

(22) Filed: Nov. 20, 2000

Related U.S. Application Data
(60) Provisional application No. 60/166,445, filed on Nov. 19, 1999.

(51) Int. Cl.[7] .............................................. G01R 27/04
(52) U.S. Cl. ..................................................... 324/639
(58) Field of Search ................................ 324/636, 637, 324/639, 640, 642, 643; 73/23.2, 28.01; 353/252

(56) References Cited

U.S. PATENT DOCUMENTS

| | | | |
|---|---|---|---|
| 3,403,335 A | | 9/1968 | Couper et al. ............... 324/645 |
| 3,500,182 A | | 3/1970 | Reed et al. .................. 324/640 |
| 4,217,565 A | * | 8/1980 | Salzberg ..................... 333/258 |
| 4,544,880 A | | 10/1985 | Nagy et al. .................. 324/642 |
| 4,651,085 A | * | 3/1987 | Sakurai et al. ......... 324/58.5 R |
| 4,902,961 A | | 2/1990 | De et al. ..................... 324/640 |
| 4,996,489 A | | 2/1991 | Sinclair ....................... 324/639 |
| 5,073,755 A | | 12/1991 | Neufeld ....................... 324/632 |
| 5,101,163 A | * | 3/1992 | Agar ........................... 324/639 |
| 5,103,181 A | | 4/1992 | Gaisford et al. ............. 324/637 |
| 5,157,340 A | * | 10/1992 | Walton et al. ............... 324/641 |
| 5,334,941 A | * | 8/1994 | King ............................ 324/637 |
| 5,741,979 A | * | 4/1998 | Arndt et al. ............. 73/861.05 |
| 5,877,663 A | * | 3/1999 | Palan et al. .................. 333/252 |
| 5,933,014 A | * | 8/1999 | Hartrumpf et al. ......... 324/642 |
| 6,037,783 A | * | 3/2000 | Reich .......................... 324/639 |
| 6,275,738 B1 | * | 8/2001 | Kasevich et al. ........... 607/101 |

FOREIGN PATENT DOCUMENTS

| | | | |
|---|---|---|---|
| DE | 27 12 600 | 9/1977 | ............. B07C/5/34 |
| GB | 976128 | 11/1964 | |
| GB | 1078111 | 8/1967 | |
| JP | 60007347 | 6/1983 | ................. 73/31.05 |
| JP | 07005122 | 6/1993 | .......... G01N/22/00 |

* cited by examiner

Primary Examiner—Safet Metjahic
Assistant Examiner—Etienne P. LeRoux
(74) Attorney, Agent, or Firm—Patrick Stellitano

(57) ABSTRACT

A novel microwave sensor (10, 60, 70, 90, 200, 250, 280) provides low-cost, robust measurement of the electrical properties of fluid substances. The sensor is suitable for use in an industrial vessel or pipe and employs parallel electrical transmission paths (12,14) that differ in electrical or physical length. The electrical length of each transmission path, which may be a two-way path caused by placing a reflective element in each path, is further determined by the electrical properties of the material under test. The frequency (f) of the signal being applied to the sensor is varied in a known manner such that the difference in the electrical lengths ($\Delta L$) of the transmission paths (12, 14) is caused to correspond to an odd integral multiple of a half wavelength. When the frequency is so adjusted and the signals that have traversed the transmission paths are allowed to coherently interfere with one another, then a minimum resultant signal or null is obtained. The null frequency for which a minimum signal is obtained is a direct measurement of the real part of the electrical permittivity ($\in_r$) of the material under test and thus provides a measurement from which material composition can be inferred. The material under test may be stationary or flowing past the probe element without affecting the characteristic of the measurement. An important application of the measurement method is that of determining the quality of steam and a preferred embodiment of such a sensor is described. Other fluid substances can be sensed using the sensor by the present inventions.

45 Claims, 7 Drawing Sheets

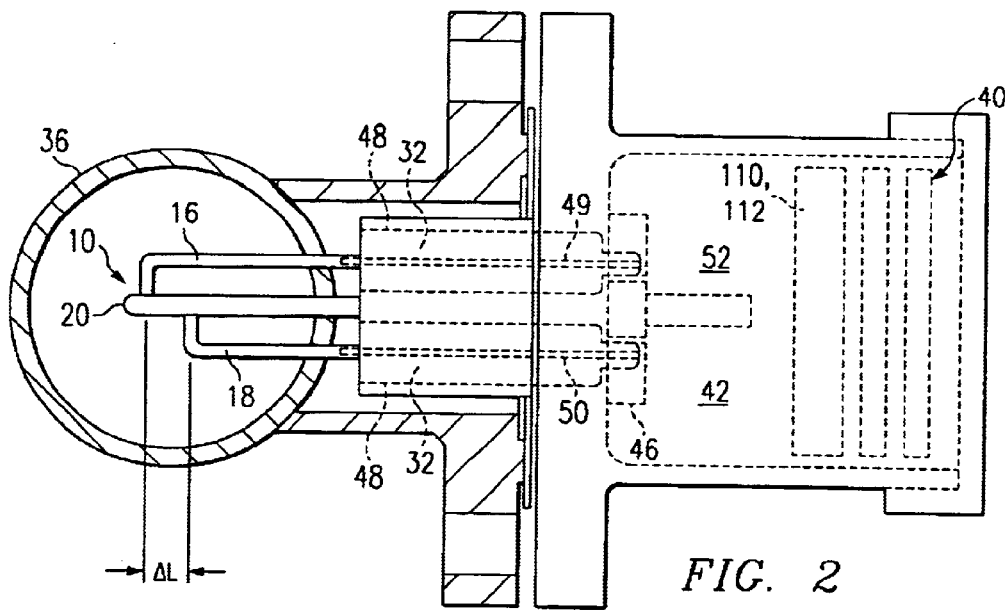
FIG. 2
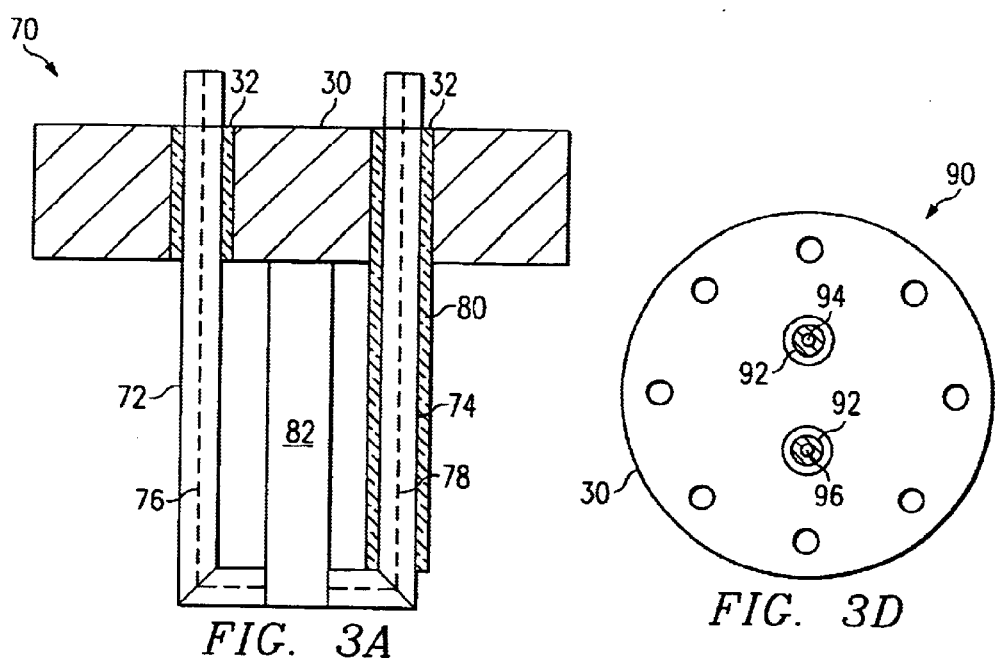
FIG. 3A
FIG. 3D

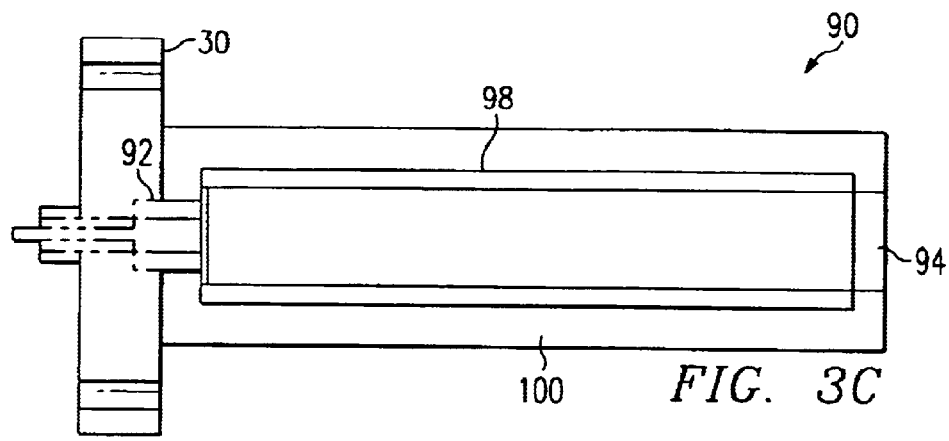
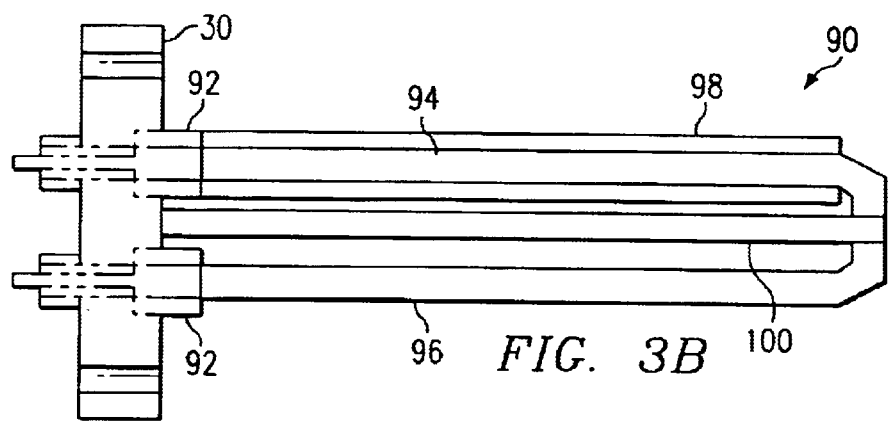
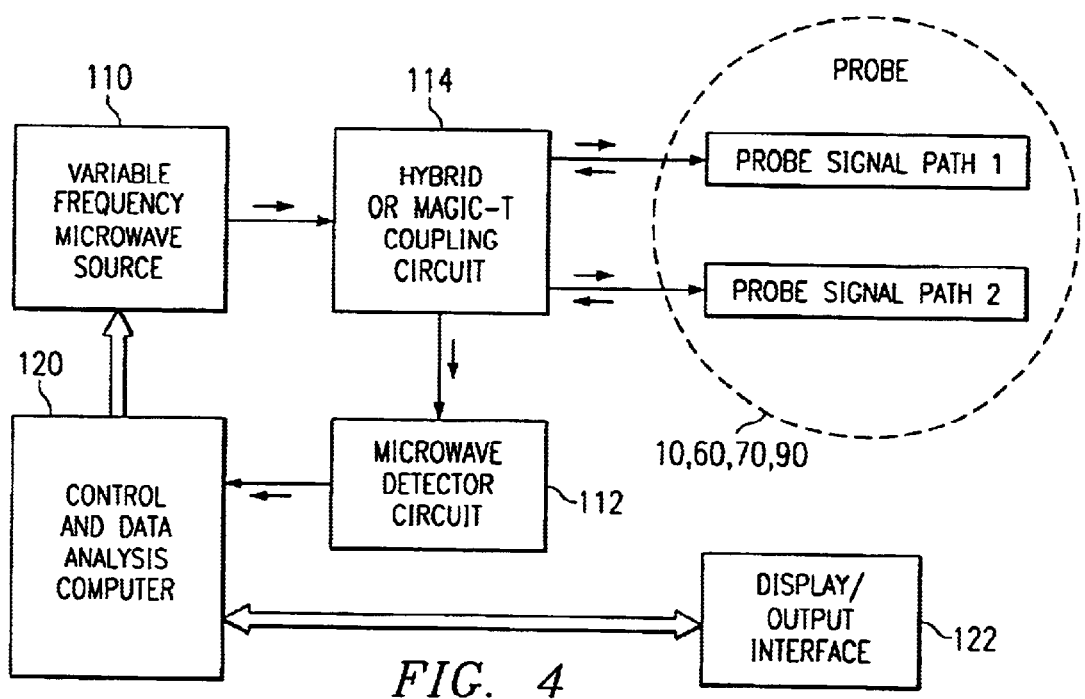

MICROWAVE SENSOR HAVING IMPROVED SENSITIVITY

PRIORITY CLAIM

Priority is claimed of commonly assigned co-pending U.S. provisional patent application, Ser. No. 60/166,445 filed Nov. 19, 1999 entitled "A Microwave Sensor", the teachings included herein by reference.

FIELD OF THE INVENTION

The present invention relates generally to the in situ measurement of the bulk electrical properties of various substances, often fluid mixtures, and the interpretation of such direct electrical measurements to produce an indirect or inferred measurement of the composition of a given substance or mixture based upon the change in electrical properties that occurs as the relative percentages of the components in the mixture vary. In some situations the invention also has application to solid substances having a surface that can be interrogated by placing the surface of a suitably configured probe against or in close proximity to the substance surface.

BACKGROUND OF THE INVENTION

The electrical permittivity of a nominally homogeneous mixture depends upon the volumetric ratio of the constituent materials and upon the permittivity of the individual components. Microwave instruments exploit this fact to analyze the properties of substances or the composition of mixtures by measuring and analyzing various attributes of a microwave signal or set of signals that depend directly upon the permittivity of the substance or mixture. For example, instruments in a variety of configurations are available which measure the attenuation or phase shift of signals that are transmitted through an unknown mixture. The material sample may be placed between transmitting and receiving antennas as described in Swanson, U.S. Pat. No. 4,812,739. Alternatively, the sample may be loaded into a coaxial or waveguide structure that supports the propagation of the wave or waves according to the inventions contained in Jean et al., U.S. Pat. No. 5,455,516; Scott et al. U.S. Pat. No. 4,862,060; or De et al. U.S. Pat. No. 4,902,961.

Likewise, prior-art reflection sensors are available which rely on measuring the amplitude and phase of the reflection coefficient at the interface between a probe element and the mixture surface. For example, see "A Novel Numerical Technique for Dielectric Measurement of Generally Lossy Dielectrics" by Ganchev, Bakhtiari, and Zorghi, IEEE Transactions on Instrumentation and Measurement, Vol. 41, No 3, June 1992. However, even the most sensitive reflection sensors cannot reliably measure the extremely small electrical differences that are associated with many important applications, such as the measurement of steam quality.

Shearer et al. teach a microwave absorption technique for analyzing gases in U.S. Pat. No. 5,507,173. This analyzer employs parallel microwave beams, but the separate beams pass through independent measurement cells and an elaborate arrangement of attenuators and signal splitters is needed to determine the difference in microwave absorption between a one cell containing a reference gas and another containing the gas under test. The analyzer operates at a single carefully controlled frequency selected to correspond to an absorption line of the gas being analyzed.

Carullo, Ferrero and Parvis in "A Microwave Interferometer System for Humidity Measurement" describe an interferometer technique for the measurement of humidity. This interferometer falls short in two important respects. First, the dynamic range of the interferometer method described by Carullo is severely limited. Secondly, Carullo describes a phase measurement being made on interfering signals that are at a constant frequency. As a consequence, the interferometer is severely limited in sensitivity and accuracy. Also, the Carullo interferometer does not allow for the measurement of the loss factor of the material.

There is a significant need for a microwave-based sensor that has sufficient precision to reliably monitor the composition of mixtures of gases, while having sufficient dynamic range to address applications where the mixtures contain large variations in moisture and the process undergoes large swings in pressure and temperature.

In addition, there is a need for a microwave sensor that can maintain a sensitive measurement as the probe element is subjected to wear or corrosion in harsh environment of the measurement zone. Additional needs include that the probe be insensitive to stray reflections and other signal artifacts that can render prior art sensor inoperative and that the probe requires very low signal power to operate. The ability to operate at very low power levels is desired to reduce the sensor cost and mitigate operational problems in satisfying FCC rules.

As an example of the need for an improved microwave sensor, consider the application of measuring the composition of a gas mixture such as encountered in the measurement of steam quality. Gases have dielectric constants very near that of free space. For example, dry steam at 110 degrees Celsius has a relative dielectric constant of 1.0126 as reported in the Handbook of Chemistry and Physics $63^{rd}$ Edition, CRC Press, Inc., 1983. Theoretical computations predict that the relative dielectric constant for 50% quality steam will increase to only 1.081. This change in dielectric constant is 6.75% for a 50% change in steam quality. It will be clear in the descriptions that follow that the present invention can easily distinguish such small changes.

SUMMARY OF THE INVENTION

The present invention achieves technical advantages as a microwave-based sensor having improved sensitivity over prior art microwave-based sensors. The sensor is rugged in construction and low in cost to produce.

One preferred embodiment of the invention is a probe-type sensing element which is insertable into a vessel or pipe and is suitable for monitoring changes in the electrical properties of steam. A sensor with improved sensitivity is required for steam quality measurement because of the relatively small change in permittivity of wet steam over a quality range as large as even from 50 to 100%. As will be evident from the discussions that follow, other configurations for the sensor that are suitable for a wide range of applications are also contemplated within the scope of the invention and examples will be given.

The sensor accomplishes a measurement by varying the frequency of the microwave excitation signal and observing when a minimum ("null") is detected for the vector sum of two output signals. The two signals travel unequal electrical distances. The vector summation will be a minimum (null) whenever the electrical traveled distances differ by a half wavelength, or an odd integral multiple of a half wavelength. It should be appreciated by those skilled in the art that the same general effect can be obtained by inverting the signal in one of the signal paths, such that the signals will produce a minimum output (null) for those frequencies for which the paths differ in length by a full wavelength or an integral multiple of a full wavelength. The electrical distance of travel is dependent upon the dielectric properties of the material under test. As the electrical permittivity (or dielectric constant, as it is commonly known) of the material mixture responds to changing amounts of its electrically different components, then the frequency required to make the electrical length difference equal to a half wavelength will also change. Determining this null frequency therefore represents a direct measurement of the dielectric constant and hence the relative composition of the mixture.

Consider some specifics of the design, for example, of a sensor for the measurement of steam quality. Such a sensor may employ a probe that has signal paths that differ by 1.5 cm in physical length. In vacuum, this path difference corresponds to a half wavelength at a frequency of approximately 10 GHz. For dry steam according to the conditions specified above, the frequency shifts to a value of 9.937589 GHz. For 50% quality steam, a frequency of 9.618353 GHz is observed, a frequency difference of more than 319 MHz. Microwave circuits are readily available which are stable to within a few parts per million and frequency measurements are easily accomplished to a similar precision. If we consider a frequency measurement accuracy of only 100 parts per million, then the 50% steam quality range can be measured to a precision of +/−0.0156% of steam quality. Certainly, there are other factors, such as temperature and pressure, that will affect the steam quality measurement, but the sensor itself clearly has sufficient precision for the task.

The null frequency value depends primarily upon the real part of the permittivity. As the signals from the two paths are combined so as to produce the null by destructive interference, the depth of the null will depend upon the amount of attenuation that the waves have experienced. Observing the depth of the null thus provides one measure of the imaginary part of the permittivity or loss factor. The total amplitude of the reflection for an off-null condition will also be indicative of the loss factor encountered by the signals. The overall length of the signal paths will influence the sensitivity of the loss factor measurement. If it is not required to measure loss factor, then only one signal path equal to a half-wavelength distance need be inserted in the process stream. It is also possible to expose only one signal path along its full length or any portion of its full length to the process while the second signal path functions simply as a fixed reference. In most applications it will be beneficial to have two signal paths inserted into the process stream so as to take advantage of common mode rejection of the effects of external parameters that are unrelated to the composition measurement.

One alternative configuration for a microwave sensor according to the teaching of the present invention is to embed the transmission lines in a dielectric material along the walls of the pipe or vessel so as to not have a probe element protruding into the process stream or vessel. Such a configuration will have less sensitivity than a probe-type sensing element, but there are many applications that can be addressed with more than enough precision owing to the inherent advantages of the invention.

Yet another configuration is to embed the transmission lines in a dielectric material and still configure the sensor as a probe element. Such a configuration would be suitable for a portable version of the instrument for applications such as the sampled measurement of the percent of fat in processed or ground meat.

Yet another configuration consistent with the teaching of the present invention is to transmit the microwave energy through the process material and to have either two transmitting elements or two receiving elements and locate them in a position such that parallel paths differing in length are formed. For this configuration, the transmitting and receiving elements are embedded in the walls of a metal pipe or vessel using suitable microwave transparent windows, or for the case of a plastic pipe or vessel, the transmitting and receiving elements are mounted on the outside of the pipe. For this configuration care must be taken to prevent the occurrence of multiple signal paths, which would potentially introduce false signals and readings.

Yet another configuration according to the present invention is to cause the process material to flow through, or to statically fill, the through arms of a rectangular waveguide hybrid-tee. An abrupt impedance mismatch is placed in each arm at distances from the center of the hybrid junction differing by a half wavelength according to the teaching of the invention described above. The excitation signal is supplied to either the E-plane or H-plane arm of the tee. The excitation signal is equally divided into the through arms of the tee and is reflected from the abrupt impedance mismatch back toward the hybrid junction. The vector summation signal will then appear at either the H-plane or E-plane arm, respectively.

BRIEF DESCRIPTION OF THE DRAWINGS

FIG. 2 illustrates some of the details of the construction of one embodiment of the process seal/microwave coupling structure suitable for a high-temperature, high-pressure application;

FIG. 3A illustrates a second configuration for a probe element in which the physical lengths of the two two-way signal paths are equal. The electrical length of one path is made longer by coating one conductor of one of the transmission lines with a dielectric material, thereby causing the velocity of propagation to be decreased;

FIG. 3B illustrates a probe similar to that shown in FIG. 3A according to another preferred embodiment;

FIG. 3C depicts a side view of the probe of FIG. 3B;

FIG. 3D is a bottom view of the probe of FIG. 3B;

FIG. 4 is a block diagram of a complete sensor assembly. The electronic circuits identified in the block diagram may be used with multiple probe configuration;

DETAILED DESCRIPTION OF THE PREFERRED EMBODIMENTS

Figure 1A:
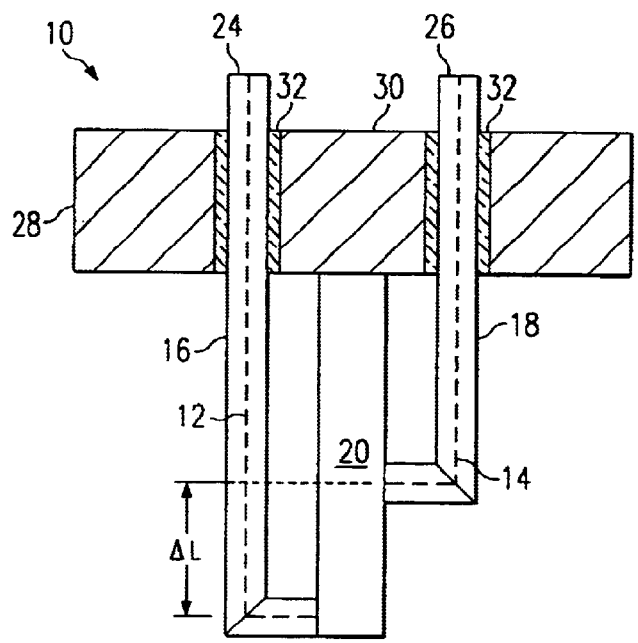
FIG. 1A depicts a probe element according to a first preferred embodiment of the present invention, where the two-way signal paths for the probe shown in FIG. 1A differ in physical length.

As used here, the term "fluid mixture" refers to any type of mixture of gas, liquid, or solid components that generally flow and conform or can be caused to conform to the shape of the mixture's container or to the surface of an inserted probe or sensing element. Although the present invention can be configured to operate at a wide range of frequencies, the primary interest here is to measure the electrical properties of the materials in the microwave portion of the electromagnetic spectrum.

In general, the term "electrical properties" refers to both the electrical permittivity and the magnetic permeability of the substance or material under investigation. Both of these material properties are described mathematically by real and imaginary terms and may be dependent upon the orientation and strength of the applied electromagnetic fields. For most applications of interest in industrial processes, only the linear scalar complex electrical permittivity comes into play. For brevity, the descriptions of the invention will assume electrical permittivity or dielectric constant to be the variable of interest. It will be understood by those skilled in the art that the descriptions could also incorporate the effects of magnetic permeability and the non-linear and tensor nature of both the electrical and magnetic parameters without altering the scope of the present invention.

The simplest structure for a probe element is shown at 10 and is configured to have two electrical paths 12 and 14 that differ in physical length, as is depicted in FIG. 1. The probe structure 10 of FIG. 1 has two image line transmission lines 16 and 18 that share a common ground plane conductor 20. Each transmission line 16 and 18 is terminated in a short circuit at the ground plane 20 so as to reflect the signal back to the source end of the probes shown at 24 and 26. The use of a reflecting termination is a convenient way to extract the signal from the probe without the need for an additional penetration into the vessel. For this configuration, if the probe 10 is inserted into a pipe 36 in which process material is flowing, the probe 10 is oriented so that the large flat surface of the ground plane member shown at 20 is parallel to the direction of flow. In this way, the process flow experiences the least restriction and both transmission lines 16 and 18 are equally exposed to the material under test. It should be appreciated by those skilled in the art that the choice of an image line configuration is only one of many possible options for the probe's transmission lines using this teaching.

The image line conductors 16 and 18 penetrate the probe's mounting flange 30 and are insulated by a dielectric material 32 that also seals the space around each conductor 16 and 18. Many dielectric materials are available which can provide a suitable dielectric value as well as a secure seal. The diameter of each conductor 16 and 18 and the dielectric seal are selected to provide adequate strength for each component and also to control the characteristic impedance of the line as it passes through the metal flange 30. The design equations for controlling the impedance of the line are well known by those skilled in the art.

The conductors 16 and 18, which exit the probe through the rear side of mounting flange 30, are connected to the probe's electronic circuits 40 (as shown in FIG. 4) either by cable or by other direct connection. A preferred embodiment and advantage of the invention is to eliminate the use of coaxial cables and associated connectors by extending the center conductors 49, 50 directly into the enclosure 46 for the microwave circuit, thereby forming a rigid integral unit. One such interface is to have the center conductor 20 extend through flange 30 and into a section of rectangular waveguide 46 in a manner similar to standard coax-to-waveguide adapters, as shown in FIG. 2. The transmission lines 16 and 18 are mounted through respective RF feedthroughs 48, as shown. This particular interface is especially well suited to high pressure applications because the dielectric material 32 of the process seal need not be penetrated by the metal conductors 49 and 50, thereby eliminating the difficult task of sealing around the conductors.

Since a waveguide interface is very convenient for sealing purposes, it also makes sense to use a waveguide hybrid-tee 46 to separate the excitation and reflected signals. The main body of the hybrid-tee 46 can be machined directly into the surface of the mounting flange 30. Such an arrangement helps to reduce the cost of the overall sensor 10 and provides an extremely robust and compact microwave interface. This arrangement works well for high temperature applications since there are no temperature critical components required as part of the hybrid-tee 46 structure. The external waveguide sections of the hybrid-tee 46 can be made to any convenient length, thereby allowing the active electronic components, such as a signal generator and the signal detector 52, to be well removed from the harsh conditions of the mounting flange 30, yet still avoiding the use of coaxial cables and the corresponding troublesome connectors.

Figure 1D:
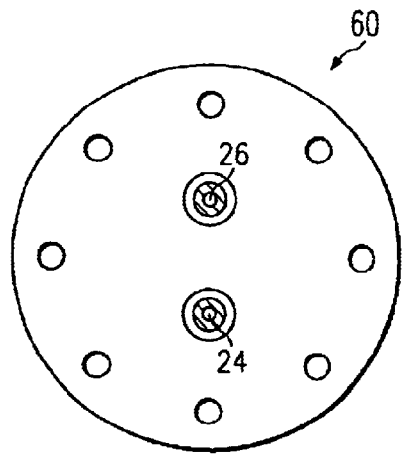
FIG. 1D depicts a bottom view of the probe of FIG. 1B.
Figure 1C:
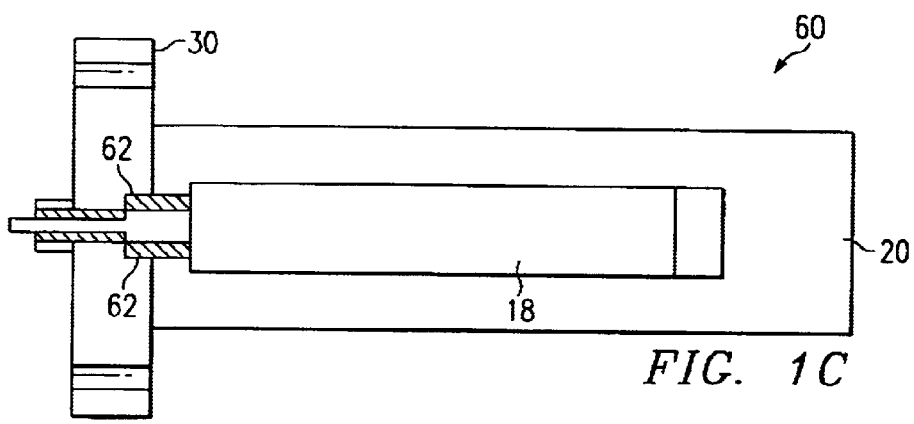
FIG. 1C depicts a side view of the probe shown in FIG. 1B.
Figure 1B:
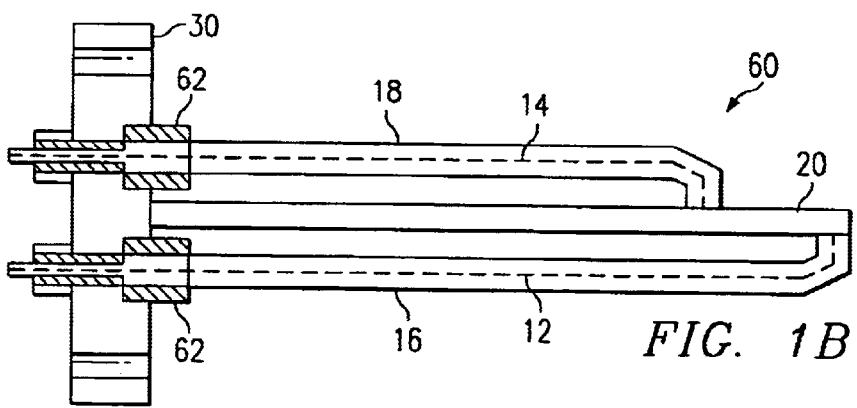
FIG. 1B depicts a probe similar to that shown in FIG. 1A according to another preferred embodiment.

FIG. 1B, FIG. 1C and FIG. 1D illustrate a modified probe 60 being similar to probe 10 of FIG. 1A, the transmission lines 16 and 18 are sealed to a mounting flange 62 by a respective dielectric mounting receptacle.

Another probe configuration 70 is shown in FIG. 3A. Again, the arrangement of the conductors 72 and 74 for the transmission lines is that of an image line structure, having a ground plane conductor 82. In this case, however, the electrical lengths of the two transmission line paths 76 and 78 are caused to differ by coating the primary conductor 74 of one of the image lines with a dielectric material 80. The presence of the dielectric material 80 around the conductor 74 will alter the velocity of propagation for the wave travelling along this path 78, hence, the electrical length of path 78 will differ the electrical length of path 76 from the non-coated probe 72. The remaining features of such a probe configuration 70 do not change from that of probe 10. The distinguishing performance feature of this particular arrangement is that the probe 10 will tend to respond to the averaged effect of the dielectric properties along the entire length of the probe transmission lines 72 and 74. The probes of FIG. 1A and FIG. 1B will tend to respond more to the dielectric properties in the differential length section "L" of the longer of the two transmission lines 16.

Yet another probe is shown at 90 in FIG. 3B, FIG. 3C and FIG. 3D having RF feedthroughs 92 for each of transmission lines 94 and 96 with a dielectric material 98 being disposed about transmission line 94, and a large common transmission line 100.

The block diagram shown in FIG. 4 shows the basic components necessary for the complete sensor to function. The system requires a variable frequency source of microwave energy 110 that can be precisely controlled. The output information derived from the sensor is the frequency at which a null condition is observed which is calculated by the sensor's detector circuit 112. Both the frequency source 110 and the detector 112 are connected to a hybrid coupler 114. The coupler 114 directs the energy from the source 110 to the two transmission paths of the probe elements, and also combines the return signal from the probe and presents it to the detector 112. The sensor operation is controlled and monitored by a suitable control and data analysis computer 120 having DSP circuitry or the like. The ultimate data from the utilized probe is directed to a display/output interface unit 122 that interfaces with the user and other control equipment.

Figure 5:
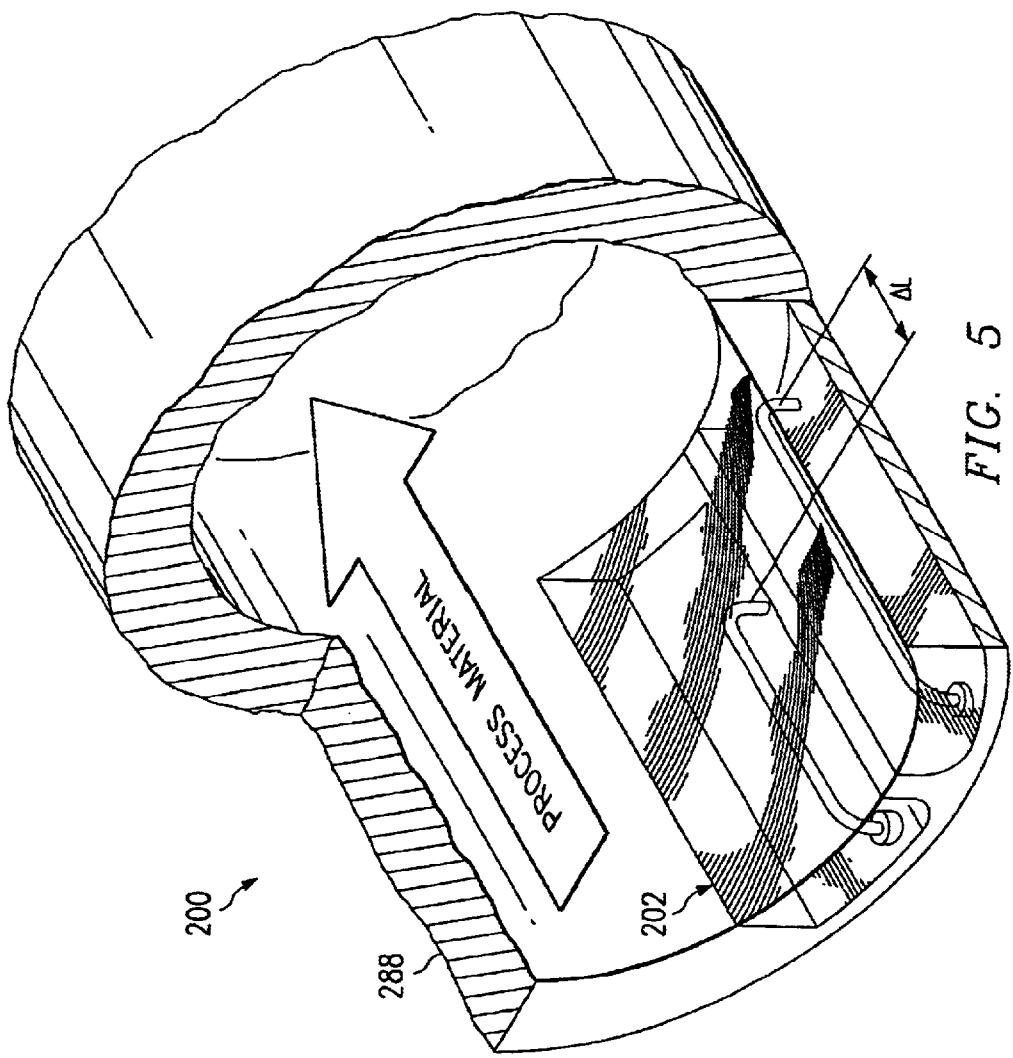
FIG. 5 shows a possible configuration for a probe mounted in the wall of a pipe or vessel.
Figure 7:
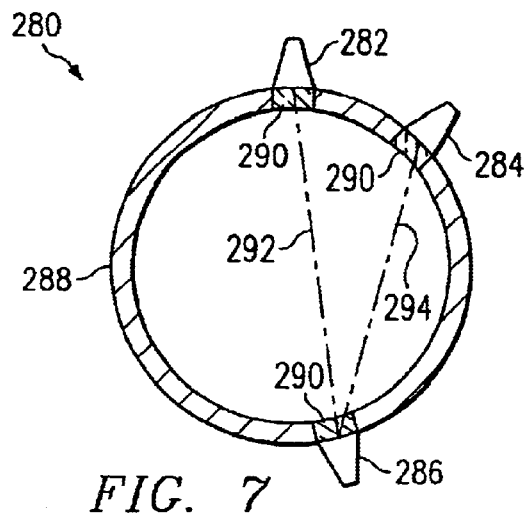
FIG. 7 shows a two-transmitter version of an embodiment of the invention that provides measurement signals that transit across the entire cross section of a process stream communicated therepast.
Figure 8:
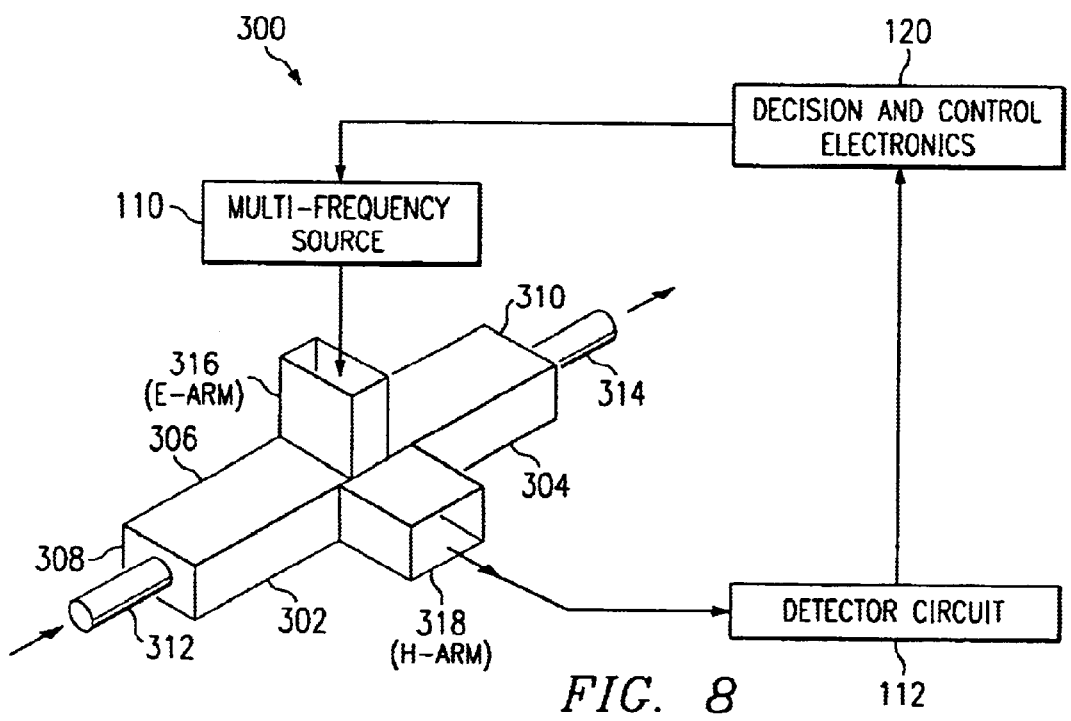
FIG. 8 depicts a waveguide structure achieving the features of the invention and through which the process material is caused to flow.

The sensor configuration 200 of FIG. 5 has several distinctive performance features. First is the appreciated fact that nothing protrudes into the process stream fluid path to restrict the flow of the process material. This non-intrusive arrangement 200 is an important technical advantage for process streams traveling at high velocities or containing a large volume of solid material. A second feature and technical advantage is that the sensor 202 is less sensitive to changes in dielectric properties and can therefore handle a wide span in properties without requiring an excessively wideband frequency source. This configuration 200 can potentially handle more highly conductive mixtures than the other sensor designs.

Figure 6:
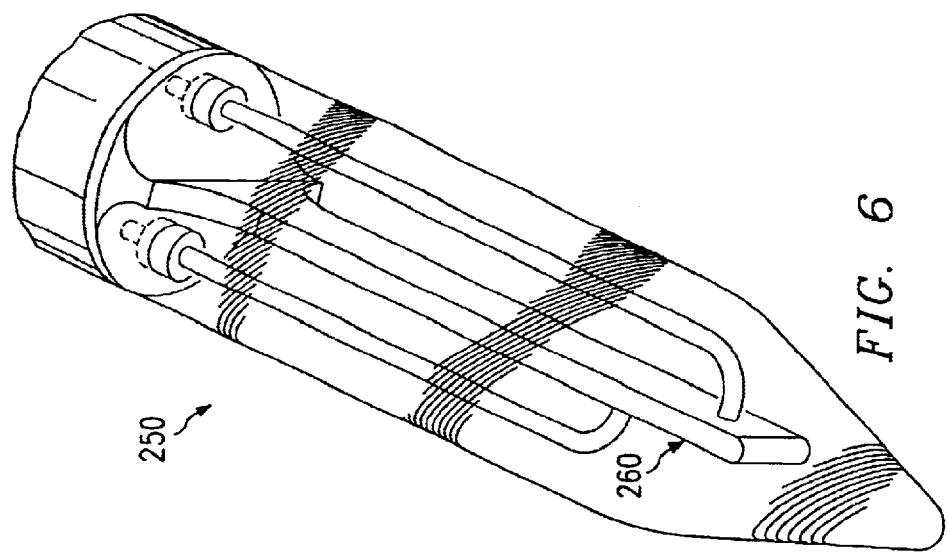
FIG. 6 illustrates a probe configuration suitable for a portable version of the invention that would lend itself to a batch-sampling instrument, having utility for such applications as processed or ground meats, batch mixed doughs and batters, etc.

Yet another configuration is to embed the transmission lines in a dielectric material and still configure the sensor as a probe element. The configuration 250 shown in FIG. 6 is that of a completely sealed probe design 260. Because the probe 260 is completely sealed, the probe 260 is less sensitive than the probe 10 shown in FIG. 1, but it will, however, still address a wide range of important applications. Probe 160 has the benefit of being suitable for a portable version of the sensor. Such a configuration would be suitable for a portable version of the instrument for applications such as the sampled measurement of the percent of fat in processed or ground meat.

Yet another configuration consistent 280 with the teaching of the present invention is to transmit the microwave energy through the process material and to have two transmitting elements 282, 284 and one receiving element 286 and locate them in a position such that signal paths 292, 294 differing in electrical length are formed. In one configuration, the transmitting 282, 284 and receiving 286 elements are embedded in the walls of a metal pipe or vessel using suitable microwave transparent windows 290. For the case of a plastic pipe or vessel, the transmitting 282, 284 and receiving 286 elements are mounted on the outside of the pipe 288. For either configuration care must be taken to prevent the occurrence of multiple signal paths, which would potentially introduce false signals and readings. It should also be noted that the signal paths 282, 284 do not have to lie in the same plane but may displaced from one another as, for example, is obtained when the transmitting elements are displaced from one another along the length of the pipe 288. A similar configurations accomplishing the same teaching, can be obtained by reversing the roles of the transmitting and receiving elements such that there would be two receiving elements and a single transmitting element.

Yet another configuration 300 according to the present invention is to cause the process material to flow through, or to statically fill, the through arms 302, 304 of a rectangular waveguide hybrid-tee 306. An abrupt impedance mismatch 308, 310 is placed in each arm at distances from the center of the hybrid junction 306 differing by a half wavelength according to the teaching of the invention described above. The excitation signal source 112 is applied to either the E-plane 316 or H-plane 318 arm of the tee. The excitation signal is equally divided into the through arms 302, 304 of the tee and is reflected from the abrupt impedance mismatch 308, 310 back toward the hybrid junction 306. The vector summation signal will then appear at either the H-plane 318 or E-plane 316 arm, respectively.

Operation of the Sensor

The operation and technical advantages of the sensor will be discussed and appreciated in terms of a specific application example, that of the measurement of steam quality. The steps needed to analyze the performance of the sensor and the descriptions of the various steps required in the measurement process, are essentially the same for any chosen application.

As a starting point in the description of the sensor operation, consider the electrical permittivity of a steam/water mixture and the resulting changes in this parameter of the steam as its quality varies. A useful mathematical expression for predicting the permittivity of the steam/water mixture is a simple mixing model, according to the following equation:

$$\varepsilon_{mix} = (\phi_1 \varepsilon_1^{1/2} + \phi_2 \varepsilon_2^{1/2})^2$$

The dielectric constant of the mixture is dependent upon the volume fraction, $\phi$, of the mixture constituents multiplied times the square root of the dielectric constant, $\in$, of that constituent added to a similar factor for each constituent in the mixture. The sum of these terms is squared to give the resulting dielectric constant of the mixture.

Steam quality is measured in terms of the mass ratio of steam to dispersed liquid water. Thus it is necessary to express steam quality in terms of volume by taking into account the density of the steam, $\rho_s$, and that of the water, $\rho_w$. Steam density is determined by temperature and pressure. Liquid water density depends on temperature. Thus for steam, a mixing equation for the dielectric constant depending upon steam quality Q is:

$$\varepsilon_Q = \left\{ \left[ \frac{Q(\rho_w/\rho_s)}{1+(\rho_w/\rho_s-1)Q} \right] \varepsilon_s^{\frac{1}{2}} + \left[ \frac{(1-Q)}{1+(\rho_w/\rho_s-1)Q} \right] \varepsilon_w^{\frac{1}{2}} \right\}^2$$

Figure 9:
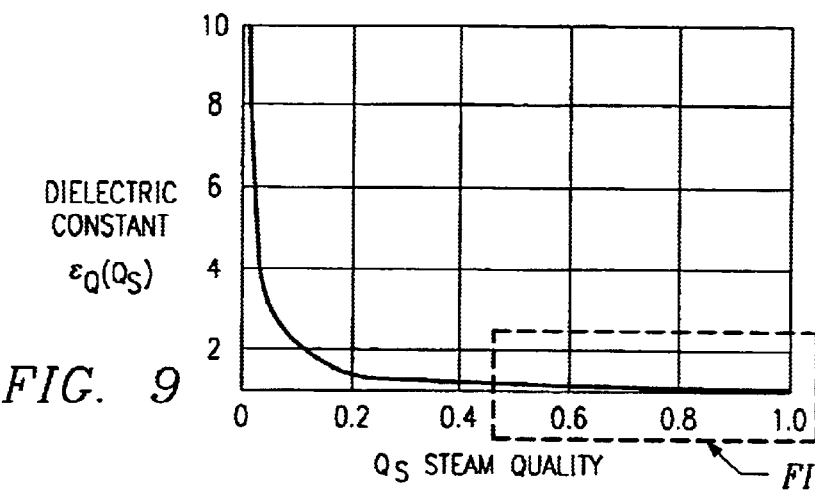
FIG. 9 depicts the dielectric constant of steam over the full range of steam quality.

For this simple analysis, consider steam at 153.010 pounds per square inch (psi). For this pressure of steam, the temperature is found to be approximately 360 degrees F. The specific volume of steam under these conditions is 2.9573. The specific volume of liquid water at this same temperature is 0.01811. Page E-57 of the *Handbook of Chemistry and Physics* gives the static dielectric constant of water as 38.21 via interpolation for these conditions. As a worst-case condition, the highest reported value of the dielectric constant of steam will be used to analyze the required sensitivity of the measurement sensor. At 100 degrees Celsius, steam is reported to have a dielectric constant of 1.0126. The value for 140 degrees C. is 1.00785. FIG. 9 is a plot of the value of $\in_Q$ for these parameter values over the entire range of steam quality from 0 to 100%.

Figure 10A:
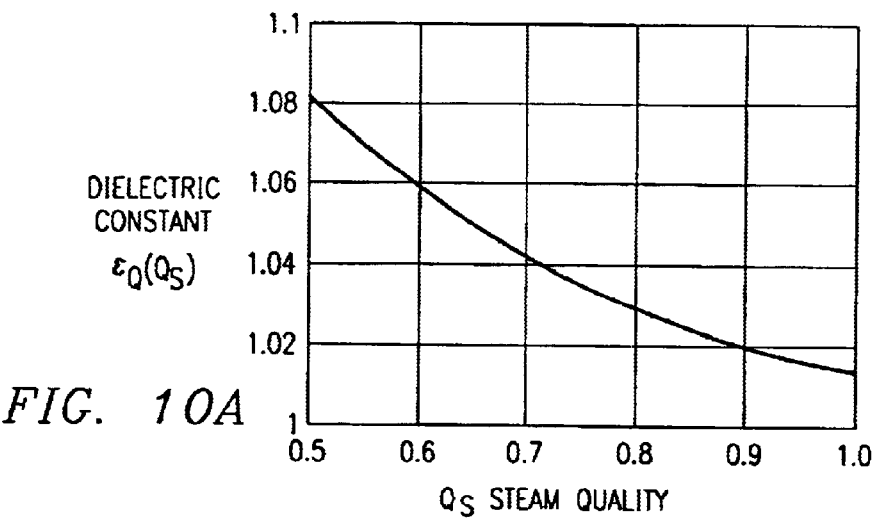
FIG. 10A expands the graph of FIG. 9 in the important range of steam quality values form 50 to 100%.
Figure 10B:
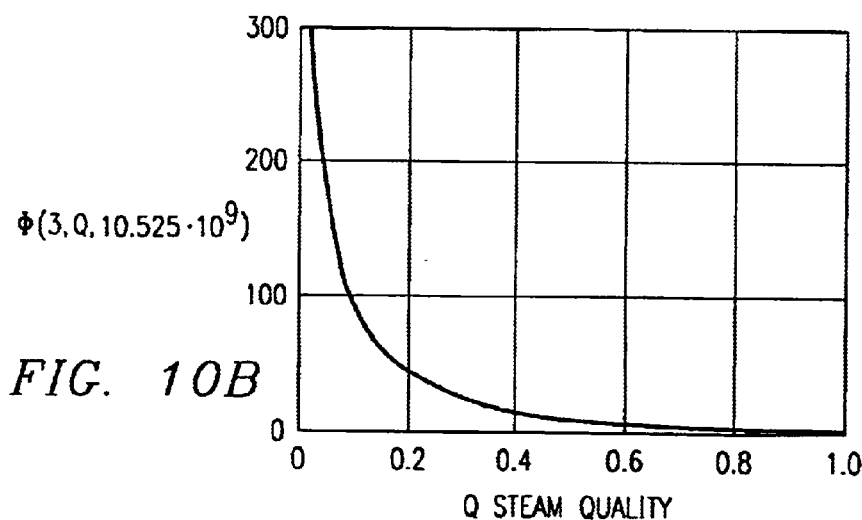
FIG. 10B illustrates the total amount of phase shift difference that can be expected for a line that is 3 inches in length of a frequency of 10.525 GHz.

One observes from FIG. 9 that the change in dielectric value for a large portion of the range in quality values, for example from 50 to 100%, is very small. FIG. 10 expands the plot over this range of quality values, and illustrates that a sensor with adequate resolution could indeed provide a measure of steam quality. Prior art microwave sensors do not have adequate resolution to make a reliable measurement of steam quality over this important range of values. Consider, for example, a sensor designed to measure dielectric constant based upon the phase shift of a wave traveling through such a steam/water mixture.

Figure 11:
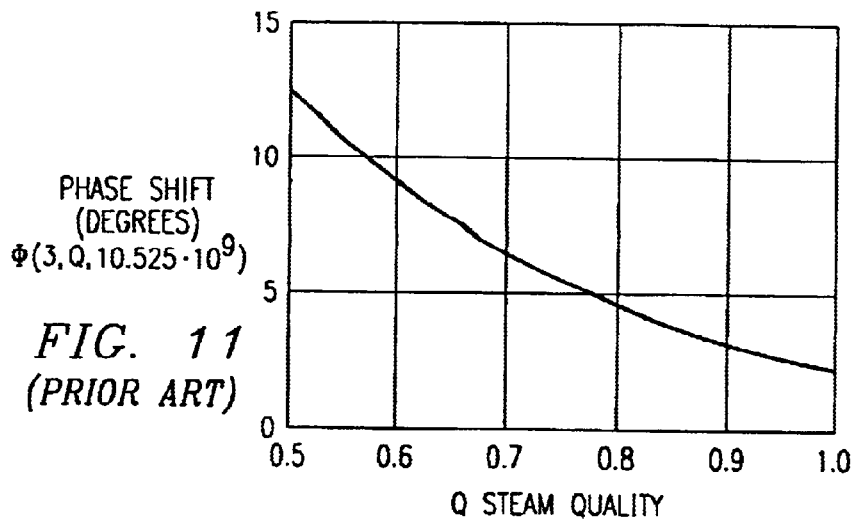
FIG. 11 is a graph of the response of a prior art phase shift sensor for the range of steam quality values shown in FIG. 10.

To compute the phase shift that would be experienced by a wave traveling along a transmission line having steam as the surrounding dielectric versus a wave traveling in free space, the amount of phase shift will depend upon the length of the line and the frequency of the energy. The graph in FIG. 11 shows the total amount of phase shift difference that can be expected for a line that is 3 inches in length at a frequency of 10.525 GHz. The graph clearly reveals to those skilled in the art that a simple phase shift measurement is not sensitive enough to do a good job of measuring steam quality in the 50% to 100% range. Phase shift measurements, at the very best, can be achieved to an accuracy of plus or minus a few degrees.

Figure 12A:
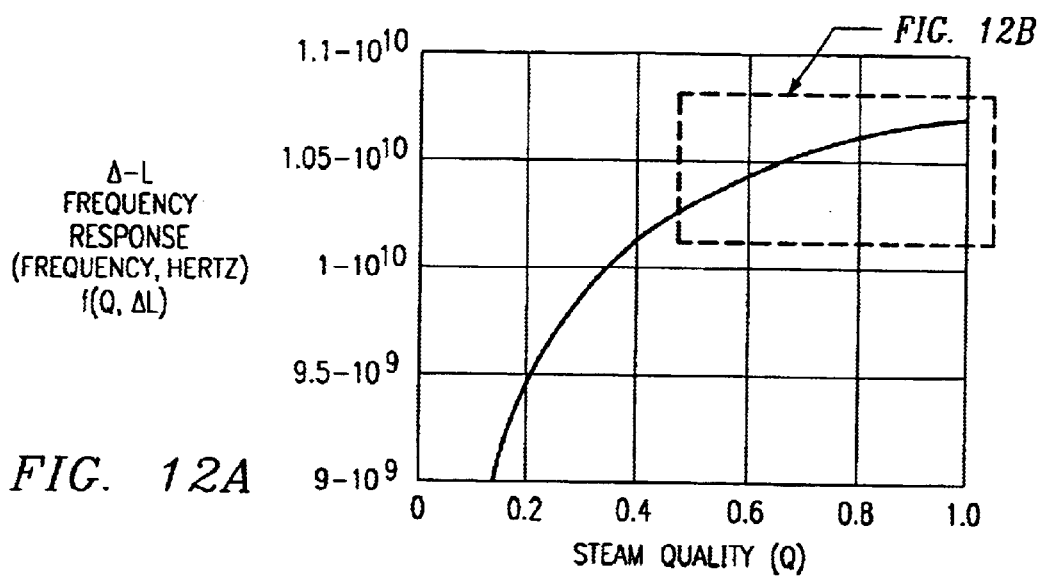
FIGS. 12A and 12B is a graph of the ΔL frequency response as a function of steam quality.
Figure 12B:
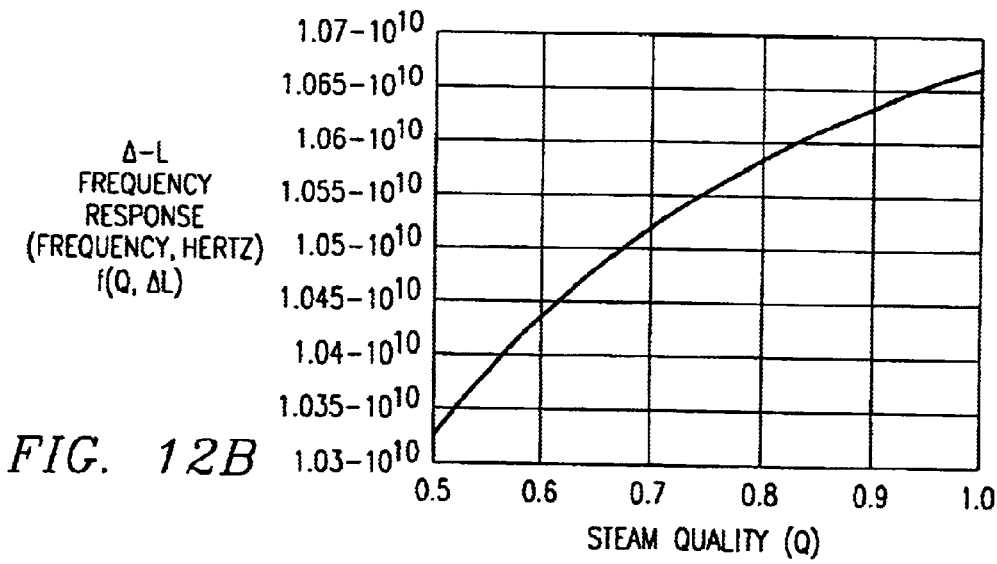

Advantageously, the total frequency shift for 50 to 100% quality steam using the sensor designed according to the present invention is shown in FIG. 12A and FIG. 12B. Those skilled in the art will readily recognize and appreciate that a very precise measurement of steam quality is afforded by measuring the "null frequency". Based upon readily available methods for generating microwave frequencies and the readily available methods for measuring such "null" frequencies, as it was shown previously, the steam quality can be measured to a precision of plus or minus 0.0156 %, a very high resolution.

Application to other Measurements

The present invention derives technical advantages by having application to a wide range of measurement problems. The preferred embodiment described, as illustrated for the steam quality sensor, is itself useful for numerous applications other than steam quality, particularly those applications for which large changes in substance properties result in relatively small changes in electrical parameters or the dielectric properties are near that of air, including wet gas measurement, gas composition measurement, bag breakout monitoring, dryer completion monitoring, moisture content in pneumatically conveyed materials, measurement of fly ash percentage in stack gases, etc. For applications involving higher dielectric constants or materials that have much larger losses associated with a signal passing through the material, other embodiments are contemplated.

The operating frequency and the difference in transmission path length may not be selected independently. Here the term "operating frequency" refers to the frequency for which a null output condition is produced for a given value of dielectric constant. If the operating frequency is given, then the transmission path length is generally fixed by the electrical properties of the material under test. A simple relationship exists between the operating frequency, $f$, and the relative dielectric constant, $\varepsilon_r$, and the difference in path length, $\Delta L$, and the number of half wavelengths, n, represented by the $\Delta L$ value according to the following equation:

$$\varepsilon_r = \left[\frac{nc}{2(\Delta L)f}\right]^2$$

where c is the speed of light in vacuum. This relationship is referred by the inventors as Delta-L($\Delta L$) technology. This expression assumes a TEM wave traveling along the transmission lines. For other modes of propagation, such as in a waveguide, the expression requires modification such that the speed of light, c, is replaced with the vacuum velocity of that particular mode.

The range in dielectric constant values that are to be measured by the sensor determines the required bandwidth of the signal source 110. Some flexibility is possible in constraining the required bandwidth. It is possible to switch in and out various lengths of transmission line to effectively adjust the phase of the signal on one of the transmission paths with respect to the other, so that the frequency required to produce the null is modified by the change in the length of the line. It is contemplated within the scope of the present invention that a lower cost version of the sensor could incorporate switchable sections of line, perhaps varying by factors of two to facilitate a digital representation of the inserted length, so that a relatively narrow bandwidth frequency source 110 could accommodate a large variation in dielectric constant for the process material under test.

It will be appreciated by those skilled in the art that many other configurations are possible which accomplish the same fundamental teaching of the present invention. Another such variation in the structure of the transmission lines is to make the insertion depth for two lines comprising a probe-type implementation to be equal, but causing the electrical lengths of the lines to differ by having one line follow a slightly serpentine path from the entry port to the end of the probe structure. Such a structure will have a response corresponding the material properties averaged along the full length of the probe, whereas two lines extending in to different depths will be more tip sensitive. Again, many options are possible for achieving the fundamental teaching and all of these are included in the choices contemplated not only for the various embodiments that are specifically mentioned in this specification, but also for those embodiments that are suggested here.

Among the potential applications contemplated for the present invention for which the teaching of the invention offers significant performance or cost advantages, in addition to the applications already noted, are the following:

Measuring any material parameter that may be inferred from measuring the electrical properties of the material.

Monitoring and controlling blending processes, for example, the mixture of gasoline with methanol, or for putting specific amounts of ether into gasoline to increase the octane, or mixing together meats having differing fat content to achieve a mixture of a specified fat value.

Measuring the moisture in powders, such as, for example, pneumatic conveying applications, grains, plastic pellets, pulverized coal and the like.

Monitoring and controlling the operation of a drying operation by measuring the moisture in the exhaust gases of a drier.

Measuring pulp stock consistency.

Measuring the concentration of various solid materials entrained in a liquid or gas.

Monitoring the purity of various pure liquids and gases.

Measuring the moisture in various food products such as doughs, batters, cheeses, and the like.

Measuring the fat content in various food products such as processed meat, ground meat, milk, and the like.

Measuring the moisture in various gases.

Measuring the moisture in hydrocarbons.

Detecting the interface between products being transported in a pipeline.

Determining the state of or percent completion of a chemical reaction.

Though the invention has been described with respect to a specific preferred embodiment, many variations and modifications will become apparent to those skilled in the art upon reading the present application. It is therefore the intention that the appended claims be interpreted as broadly as possible in view of the prior art to include all such variations and modifications. The overall length of the signal paths will influence the sensitivity of the loss factor measurement. If it is not required to measure loss factor, then only one signal path equal to a half-wavelength distance need be inserted in the process stream. It is also possible to expose only one signal path along its full length or any portion of its full length to the process while the second signal path functions simply as a fixed reference.

We claim:

1. A sensor employing electromagnetic energy for processing a substance, comprising:
   a first signal path adapted to communicate electromagnetic energy through the substance along the first path and having a first electrical distance and a first physical length;
   a second signal path adapted to communicate electromagnetic energy along the second path having a second electrical distance and a second physical length, said second electrical distance being different by a dimension ΔL from said first electrical distance;
   a boundary interposed between and along a portion of said first signal path and said second signal path and affecting a distribution of electromagnetic energy along the first and second paths;
   a signal generator electrically coupled to both said first signal path and said second signal path and generating an excitation signal at different frequencies, said excitation signal for producing electromagnetic energy communicable through the substance; and
   a signal detector electrically coupled to both said first signal path and said second signal path adapted to detect a signal resulting from electromagnetic energy communicated through the substance; said resulting signal exhibiting a characteristic indicative of the difference in said first and second electrical distances as influenced by the substance.

2. The sensor of claim 1 wherein said characteristic is a null occurring at a frequency dependent upon said difference in electrical distances.

3. The sensor of claim 2 wherein said null frequency is a function of a dielectric constant of the substance.

4. The sensor of claim 1, wherein the resulting signal further exhibits a characteristic indicative of absorption of electromagnetic energy by the substance.

5. The sensor of claim 1, wherein the resulting signal exhibits a characteristic indicative of a permeability exhibited by the substance.

6. The sensor of claim 1, wherein said first signal path comprises a first conductor disposed along said first signal path and proximate to said boundary.

7. The sensor of claim 6, wherein the first conductor terminates on the boundary.

8. The sensor of claim 6, wherein said second signal path comprises a second conductor disposed along said second signal path and proximate to said boundary.

9. The sensor of claim 8, wherein the second conductor terminates on the boundary.

10. The sensor of claim 1, wherein the boundary is electrically connected to a ground plane of the sensor.

11. The sensor of claim 1, wherein a portion of said first physical length has a dielectric material disposed thereabout.

12. The sensor of claim 11, wherein said first and second physical lengths are substantially equal.

13. The sensor of claim 1, wherein portions of said first and second physical lengths are disposed in dielectric material and disposed to communicate electromagnetic energy through the dielectric material and through the substance along the first and second signal paths.

14. The sensor of claim 13, wherein said embedded portion of the sensor forms a probe that is removably insertable into the substance through a surface of the substance exposed to a surrounding environment.

15. The sensor of claim 1, wherein the first signal path comprises a conductor extending through a solid dielectric in an aperture in the wall of a vessel containing the substance to be processed forming a process seal substantially preventing the substance to escape from the vessel through the aperture and preventing matter in an environment exterior to the vessel from entering therein through the aperture.

16. The sensor of claim 15, wherein said process seal substantially prevents steam from escaping through the aperture from the vessel, the dielectric constant selected and the aperture dimensioned so as to couple microwave energy to an enclosure into which the signal path extends, with said enclosure dimensioned to enable propagation of microwave energy therein.

17. The sensor of claim 1, wherein said first signal path comprises a first conductor and said second signal path comprises a second conductor; said first and second conductors extending through a wall of a vessel containing the substance into an enclosure coupled to the detector and generator.

18. The sensor of claim 17, wherein the enclosure comprises a hybrid-tee for coupling energy from and to the first and second signal paths to the generator and detector.

19. The sensor of claim 18 wherein the hybrid-tee is mounted to a flange through which the conductors extend.

20. The sensor of claim 17, wherein the conductors extend into the enclosure through a flange.

21. The sensor of claim 1, wherein the signal detector further comprises a first receiver for receiving a signal from the first signal path and a second receiver for receiving a signal from the second signal path.

22. The sensor of claim 1, wherein the signal generator further comprises a first transmitter for transmitting a signal to the first signal path and a second transmitter for transmitting a signal to the second signal path.

23. A method of employing electromagnetic energy to sense a characteristic of a substance, comprising the steps of:
   providing a first signal path adapted to communicate electromagnetic energy through the substance along the first path and having a first electrical distance and a first physical length;
   providing a second signal path adapted to communicate electromagnetic energy along the second path having a second electrical distance and a second physical length, said second electrical distance being different by a dimension ΔL from said first electrical distance;
   providing a boundary interposed between and along a portion of said first signal path and said second signal path and affecting a distribution of electromagnetic energy along the first and second paths;
   providing a signal generator electrically coupled to both said first signal path and said second signal path and generating an excitation signal at different frequencies, said excitation signal for producing electromagnetic energy communicable through the substance; and providing a signal detector electrically coupled to both said first signal path and said second signal path adapted to detect a signal resulting from electromagnetic energy communicated through the substance; said resulting signal exhibiting a characteristic indicative of the difference in said first and second electrical distances as influenced by the substance.

24. The method of claim 23 wherein the resulting signal further exhibits a characteristic indicative of absorption of electromagnetic energy by the substance.

25. The method of claim 23, wherein the resulting signal exhibits a characteristic indicative of a permeability exhibited by the substance.

26. The method of claim 23, wherein said first signal path comprises a first conductor disposed along said first signal path and proximate to said boundary.

27. The method of claim 26, wherein said second signal path comprises a second conductor disposed along said second signal path and proximate to said boundary.

28. The method of claim 27, wherein the first and second conductors terminate on the boundary.

29. The method of claim 28, wherein the boundary is electrically connected to a ground plane of the sensor.

30. The method of claim 26, wherein the first conductor terminates on the boundary.

31. The method of claim 23, wherein a portion of said first physical length has a dielectric material disposed thereabout.

32. The method of claim 31, wherein said first and second physical lengths are substantially equal.

33. The method of claim 23, wherein portions of said first and second physical lengths are disposed in dielectric material and disposed to communicate electromagnetic energy through the dielectric material and through the substance along the first and second signal paths.

34. The method of claim 33, wherein said embedded portion of the sensor forms a probe that is removably insertable into the substance through a surface of the substance exposed to a surrounding environment.

35. The method of claim 23, wherein the first signal path comprises a first conductor extending through a first solid dielectric in a first aperture in a wall of a vessel containing the substance to be processed forming a first process seal.

36. The method of claim 35, wherein the second signal comprises a second conductor extending through a second solid dielectric in a second aperture in the wall of a vessel containing the substance to be processed forming a second process seal.

37. The method of claim 23, wherein said first signal path comprises a conductor extending through a wall of a vessel containing the substance into an enclosure coupled to the detector and generator.

38. The method of claim 37, wherein the enclosure comprises a hybrid-tee for coupling energy from and to the first and second signal paths.

39. A method of employing electromagnetic energy to sense a characteristic of a substance, comprising the steps of:
providing a hybrid-tee with a first branch and a second branch;
the first branch providing a first signal path adapted to communicate electromagnetic energy through the substance along the first path and having a first electrical distance and a first physical length; said first branch providing an impedance boundary at an end;
the second branch providing a second signal path adapted to communicate electromagnetic energy along the second path having a second electrical distance and a second physical length, said second electrical distance being different by a dimension $\Delta L$ from said first electrical distance; said second branch providing an impedance boundary at an end;
providing a signal generator electrically coupled to both said first signal path and said second signal path through a third branch of the hybrid-tee and generating an excitation signal at different frequencies, said excitation signal for producing electromagnetic energy communicable through the substance; and
providing a signal detector electrically coupled to both said first signal path and said second signal path through a fourth branch of the hybrid-tee and adapted to detect a signal resulting from electromagnetic energy communicated through the substance; said resulting signal exhibiting a characteristic indicative of the difference in said first and second electrical distances as influenced by the substance.

40. A sensor employing electromagnetic energy for processing a substance, comprising:
a first signal path comprising a first conductor disposed along said first signal path; said first signal path adapted to communicate electromagnetic energy through the substance along the first path and having a first electrical distance and a first physical length;
a second signal path adapted to communicate electromagnetic energy along the second path having a second electrical distance and a second physical length, said second electrical distance being different by a dimension $\Delta L$ from said first electrical distance;
a conducting boundary disposed along a portion of said first signal path and affecting a distribution of electromagnetic energy along the first signal path; with said first conductor terminating on said boundary;
a signal generator electrically coupled to both said first signal path and said second signal path and generating an excitation signal at different frequencies, said excitation signal for producing electromagnetic energy communicable through the substance; and
a signal detector electrically coupled to both said first signal path and said second signal path adapted to detect a signal resulting from electromagnetic energy communicated through the substance; said resulting signal exhibiting a characteristic indicative of the difference in said first and second electrical distances as influenced by the substance.

41. The sensor of claim 40, wherein said second signal path comprises a second conductor disposed along said second signal path and proximate to said boundary.

42. The sensor of claim 41, wherein the second conductor terminates on the boundary.

43. The sensor of claim 40, wherein the boundary is electrically connected to a ground plane of the sensor.

44. The sensor of claim 40, wherein the boundary extends through an aperture in the wall of a vessel containing the substance into an enclosure.

45. The sensor of claim 44, wherein the enclosure forms a hybrid-tee coupled to said first and second signal paths.

* * * * *